(12) United States Patent
Fox

(10) Patent No.: US 8,071,101 B2
(45) Date of Patent: Dec. 6, 2011

(54) ANTIBODY THERAPY FOR TREATMENT OF DISEASES ASSOCIATED WITH GLUTEN INTOLERANCE

(75) Inventor: Barbara S. Fox, Wayland, MA (US)

(73) Assignee: Avaxia Biologics, Inc., Lexington, MA (US)

( * ) Notice: Subject to any disclaimer, the term of this patent is extended or adjusted under 35 U.S.C. 154(b) by 937 days.

(21) Appl. No.: 11/591,843

(22) Filed: Nov. 2, 2006

(65) Prior Publication Data

US 2007/0184049 A1    Aug. 9, 2007

Related U.S. Application Data

(60) Provisional application No. 60/733,061, filed on Nov. 3, 2005.

(51) Int. Cl.
*A61K 39/395* (2006.01)

(52) U.S. Cl. ................ 424/156.1; 424/157.1; 424/130.1

(58) Field of Classification Search ......................... None
See application file for complete search history.

(56) References Cited

U.S. PATENT DOCUMENTS

2004/0047856 A1    3/2004    Williams et al.

FOREIGN PATENT DOCUMENTS

WO    2005/099753 A1    10/2005

OTHER PUBLICATIONS

Warny, M., et al., "Bovine Immunoglobulin Concentrate—*Clostridium difficile* Retains *C difficile* Toxin Neutralising Activity After Passage Through the Human Stomach and Small Intestine," Gut, 44: 212-217 (1999).
Bernassola, Francesca, et al., "Role of Transglutaminase 2 in Glucose Tolerance: Knockout Mice Studies and a Putative Mutation in a MODY Patient," The FASEB Journal, 16: 1371-1378 (2002).
Shan, Lu, et al., "Structural Basis for Gluten Intolerance in Celiac Sprue," Science, 297: 2275-2279 (2002).
Arentz-Hansen, E H, et al., "Production of a Panel of Recombinant Gliadins for the Characterisation of T Cell Reactivity in Coeliac Disease," Gut, 46: 46-51 (2000).
Ellis, H J, et al., "Measurement of Gluten Using a Monoclonal Antibody to a Coeliac Toxic Peptide of a Gliadin," Gut, 43: 190-195 (1998).
Jabri, Bana, et al., "Innate and Adaptive Immunity: the Yin and Yang of Celiac Disease," Immunological Reviews, 206: 219-231 (2005).
Green, Peter H.R., et al., "Celiac Disease," Annu. Rev. Med., 57: 14.1-14.15 (2006).
Freedman, Daniel J., et al., "Milk Immunoglobulin with Specific Activity Against Purified Colonization Factor Antigens Can Protect Against Oral Challenge with Enterotoxigenic *Escherichia coli*," J. Infectious Diseases, 177: 662-7 (1998).
Ontsouka, C.E., et al., "Fractionized Milk Composition During Removal of Colostrum and Mature Milk," J. Dairy Sci., 86: 2005-2011 (2003).
Mitra, AK, et al., "Hyperimmune Cow Colostrum Reduces Diarrhoea Due to Rotavirus: a Double-Blind, Controlled Clinical Trial," Acta Paediatr., 84: 996-1001 (1995).
Matysiak-Budnik, Tamara, et al., "Limited Efficiency of Prolyl-Endopeptidase in the Detoxification of Gliadin Peptides in Celiac Disease," Gastroenterology, 129: 786-796 (2005).
Tacket, Carol O., et al., "Efficacy of Bovine Milk Immunoglobulin Concentrate in Preventing Illness After *Shigella flexneri* Challenge," Am. J. Trop. Med. Hyg., 47(3): 276-283 (1992).
Shin, Ji-Hyun, et al., "Production of Anti-*Helicobacter pylori* Urease-Specific Immunoglobulin in Egg Yolk Using an Antigenic Epitope of *H. pylori* Urease," J. Medical Microbiology, 53: 31-34 (2004).
Sarker, Shafiqul A., et al., "Randomized, Placebo-Controlled, Clinical Trial of Hyperimmunized Chicken Egg Yolk Immunoglobulin in Children with Rotavirus Diarrhea," J. Pediatric Gastroenterology and Nutrition, 32(1): 19-25 (2001).
Weiss, Joseph B., et al., "Gluten-Sensitive Enteropathy," J. Clin. Invest., 72: 96-101 (1983).
Ungar, Beth L.P., et al., "Cessation of *Cryptosporidium*-Associated Diarrhea in an Acquired Immunodeficiency Syndrome Patient After Treatment with Hyperimmune Bovine Colostrum," Gastronenterology, 98: 486-489 (1990).
Kovacs-Nolan, Jennifer and Mine, Yoshinori, "Microencapsulation for the Gastric Passage and Controlled Intestinal Release of Immunoglobulin Y," J. Immunological Methods, 296: 199-209 (2005).
Maiuri, Luigi, et al., "Association Between Innate Response to Gliadin and Activation of Pathogenic T Cells in Coeliac Disease," The Lancet, 362: 30-37 (2003).
Aleanzi, Mabel, et al., "Celiac Disease: Antibody Recognition against Native and Selectively Deamidated Gliadin Peptides," Clinical Chem., 47(11): 2023-2028 (2001).

*Primary Examiner* — Sharon Wen

(74) *Attorney, Agent, or Firm* — Elmore Patent Law Group, PC; Darlene A. Vanstone; Carolyn S. Elmore

(57) ABSTRACT

The present invention includes a pharmaceutical compositions and methods for treating diseases associated with gluten intolerance in a patient, comprising: administering to the patient an effective amount of an antibody having specific activity against gluten or gluten-derived peptides. Such diseases include, for example, celiac disease and dermatitis herpetiformis.

10 Claims, No Drawings

ANTIBODY THERAPY FOR TREATMENT OF DISEASES ASSOCIATED WITH GLUTEN INTOLERANCE

RELATED APPLICATION

This application claims the benefit of U.S. Provisional Application No. 60/733,061, filed on Nov. 3, 2005. The entire teachings of the above application are incorporated herein by reference.

FIELD OF THE INVENTION

This invention relates to the treatment of diseases associated with gluten intolerance, including celiac disease and dermatitis herpetiformis, by administration of specific antibodies in the form of oral compositions.

BACKGROUND OF THE INVENTION

Celiac disease, also known as Celiac Sprue, is a multifactorial inflammatory disease of the small intestine that affects approximately 1% of the population. There is a genetic component to the disease, and an autoimmune component, but the triggering cause of celiac disease is the response to gluten proteins and peptides derived therein. In susceptible individuals, ingestion of gluten leads to the stimulation of T cells specific for gluten-derived peptides and the induction of an inflammatory response.

Dermatitis herpetiformis is a dermatologic disorder that is also controllable by limiting intake of gluten. Therefore, treatments for celiac disease may also be useful for treatment of dermatitis herpetiformis.

Celiac disease typically presents with diarrhea, but it also presents with failure to thrive in young children, anemia, neurological problems, and osteoporosis (Green, P H R and Jabri, B. Celiac disease. *Annu. Rev. Med.* 57:14.1-14.15 (2006) (pre-publication online)). Some patients have atypical presentations or are asymptomatic. However, even among asymptomatic patients, nutritional deficiencies can develop.

Relatives of celiac disease patients are at increased risk of developing celiac disease. Celiac disease is diagnosed by testing for the presence of IgA endomysial and tissue transglutaminase antibodies. A definitive diagnosis requires a biopsy of the upper small intestine. The characteristics of celiac disease include villous atrophy, crypt hyperplasia, and intraepithelial lymphocytosis. A positive clinical effect of gluten withdrawal from the diet is also used in the diagnosis of the disease.

Celiac disease can be effectively controlled by rigorously excluding gluten from the diet. However, maintaining a gluten-free diet is very difficult because of the ubiquity of gluten-containing products. Gluten is an integral component of wheat, barley and rye. Gluten is frequently present in small amounts, even in products that are not primarily grain-based. Maintaining a strict gluten-free diet is difficult and expensive. Therefore, there is a need for products that can be used to reduce the exposure of celiac disease patients to the toxic effects of gluten.

Gluten proteins are the storage proteins found in wheat, rye and barley grains. The gluten proteins are encoded by at least 100 genes (Jabri, B, Kasarda, D D, and Green, P H R. Innate and adaptive immunity: the Yin and Yang of celiac disease. *Immunol. Rev.* 206:219-231(2005)).

Wheat gluten is isolated from wheat flour by working wheat flour dough under a stream of water. The starch fraction is washed away, leaving gluten. This preparation normally containing about 75% by weight protein, 8% by weight lipid, and with the remainder being ash, fiber and residual starch. Although a gluten ball cannot be washed from rye or barley flour doughs, the celiac disease community calls the proteins derived from rye and barley gluten, because they are close in amino acid sequence to gluten proteins of wheat and because they are active in celiac disease.

There are two major components of gluten, the gliadins, which are monomeric proteins, and the glutenins, which are polymeric proteins bound together by disulfide bonds.

Gliadin is a single-chained protein having an average molecular weight of about 30,000-40,000, with an isoelectric of pH 4.0-5.0. There are four classes of gliadin proteins: α-gliadin, β-gliadin, γ-gliadin, and ω-gliadin. Gliadin proteins are extremely sticky when hydrated and have little or no resistance to extension. Gliadin is responsible for giving gluten dough its characteristic cohesiveness. Glutenin is a larger, multi-chained protein with an average molecular weight of about 3,000,000 ranging from 100,000 to several million. The isoelectric pH of glutenin is about 6.5-7.0. The glutenin fraction is broken down into two main classes, the high-molecular-weight glutenin subunits and the low-molecular-weight glutenin subunits. Glutenin is resistant to extension and is responsible for the elasticity of gluten dough.

Generally, wheat gluten is fractionated into gliadin and glutenin proteins by initially solubilizing the gluten in dilute acid and then adding ethanol until a 70% solution is achieved. The solution is then neutralized with base and left to stand overnight at refrigeration temperatures. The ethanol-soluble gliadins go into solution while the glutenins precipitate out. Final separation involves decantation or centrifugation to yield the separate proteinaceous fractions (from U.S. Pat. No. 5,610,277). Alternatively, U.S. Pat. No. 5,610,277 describes an alcohol-free method for separating gliadin and glutenin. Therefore, the methods used to separate and define the wheat fractions of gluten, gliadin and glutenin are well understood in the art. Both wheat gluten and wheat gliadin can be purchased from SigmaAldrich.

The pathogenesis of celiac disease is fairly well understood. Gluten proteins are poorly digested by humans due to the large number of proline and glutamine residues, resulting in the presence of intact peptides in the small intestine. The peptides are deamidated by tissue transglutaminase 2, generating negatively charged peptides. The negatively charged peptides bind to HLA-DQ2 or HLA-DQ8, the HLA types most strongly associated with celiac disease, and stimulate T cells. Furthermore, the deamidated gluten peptides appear to activate the non-specific innate immune response, generating an inflammatory response. All classes of gliadin and glutenin proteins are apparently harmful to celiac disease patients (Jabri, B, Kasarda, D D, and Green, P H R. Innate and adaptive immunity: the Yin and Yang of celiac disease. *Immunol. Rev.* 206:219-231 (2005)). All of the gliadin and glutenin proteins contain large numbers of prolines and glutamines.

Although there are no therapies available for celiac disease, there are several therapies in early stages of development. These therapies are based on what is known about the pathogenesis of celiac disease.

Inhibitors of tissue transglutaminase 2 have been proposed as therapies for diseases related to gluten intolerance (see US patent applications 20040167069 and 20060035838). It is believed that these inhibitors would block the ability of the enzyme to deamidate glutamine residues in gluten or gluten-derived peptides, thus blocking the resulting immune activation. However, animals in which transglutaminase 2 has been selectively inactivated display impaired glucose-stimulated insulin secretion (Bemassola, F, et al., Role of transglutaminase 2 in glucose tolerance: knockout mice studies and a putative mutation in a MODY patient. *FASEB J.* 16: 1371-1378 (2002)). Therefore, drugs inactivating this enzyme may be found to have serious health consequences and it is desirable to find more benign means of treating celiac disease.

A second approach that is being considered to treat celiac disease is to use a peptide or peptidomimetic that will bind to HLA-DQ and prevent the binding of the gluten-derived peptide and thus the resulting activation of the gluten-specific T cell response (see US patent application 20050256054). However, this approach, if successful, might be expected to have more general immunosuppressive activity. Each individual has a limited number of HLA molecules that are used to present the universe of peptides to the individual's T cells. It is possible that the dominant T cell response to a pathogen in a given individual will be restricted by the HLA-DQ allele blocked by the inhibitory peptide, thus inhibiting the protective immune response. Therefore, it is desirable to find a therapy for celiac disease that does not create the possibility of untoward immunosuppression.

A third approach that is being considered is to use an enzyme or mixture of enzymes to break down gluten in the digestive tract. The enzyme that is most widely discussed is prolyl endopeptidase, but other enzymes have been considered as well (see US patent application 20030215438). Although enzymes have been shown to degrade gluten in a variety of settings, doubts have been raised about the potential effectiveness of the enzyme in vivo. In particular, it has been suggested that the kinetics of degradation may not be sufficient to be effective in vivo, and that the enzyme will not be active as it moves through the acidic environment of the stomach (Matysiak-Budnik, T, et al. Limited efficiency of prolyl-endopeptidase in the detoxification of gliadin peptides in celiac disease. *Gastroenterology* 129:786-96 (2005)). Furthermore, the activity of the enzyme may be affected by the pH of the food in which the gluten is ingested. Therefore, there is a need for a therapy that will be more predictably effective in blocking the toxicity of gluten and gluten-derived peptides.

SUMMARY OF THE INVENTION

The present invention includes a method of treating diseases associated with gluten intolerance in humans, comprising: administering to said human an effective amount of an antibody having specific activity against gluten or gluten-derived peptides. Such diseases include, for example, celiac disease and dermatitis herpetiformis.

A second aspect of the present invention is a pharmaceutical composition for use in treatment of diseases associated with gluten intolerance in humans including, for example, celiac disease and dermatitis herpetiformis, in a patient, comprising: an effective amount of an antibody in combination with a pharmaceutically acceptable carrier adapted for oral administration, the antibody having specific activity against gluten and gluten-derived peptides.

DETAILED DESCRIPTION OF THE INVENTION

This invention describes the development and use of antibodies directed against gluten to protect celiac disease patients from the toxic effects of gluten. The term "antibody," as used herein, refers to immunoglobulin molecules and immunologically active portions of immunoglobulin molecules, i.e., molecules that contain an antigen binding site that immunospecifically binds an antigen. Without limiting the invention by mechanism, such antibodies could alter the uptake of gluten and gluten peptides in celiac patients, could inhibit the deamidation of gluten or gluten peptides by tissue transglutaminase, or could inhibit the activation of the innate immune response by gluten peptides.

Either monoclonal or polyclonal antibodies could be used in this invention. Monoclonal antibodies are more controllable, but their specificity is limited. Monoclonal antibodies can be prepared using techniques that are standard in the literature. Polyclonal antibodies are more difficult to characterize, but their broad specificity means that they can interfere with gluten in several different ways and can interact with different classes of gluten proteins and different allelic versions of gluten. In addition, their manufacture can be very inexpensive.

Both monoclonal and polyclonal antibodies against gluten and a gluten-derived peptide have been described (Ellis, H J, et al., P J Measurement of gluten using a monoclonal antibody to a coeliac toxic peptide of A gliadin. *Gut.,* 43:190-95 (1998)), thus their production in small animals (mice and rabbits) is well understood. Preferred protein immunogens of the invention include whole gluten preparations, purified gliadins or purified glutenin. Such proteins can be purified from flour from many different wheat cultivars, including but not limited to, the Kolibri, Yamhill, Scout 66, Cheyenne, Floke or Tjalve cultivars or from flour from blended wheat preparations. Methods for purifying gluten, gliadin and glutenins are well known in the literature. Recombinant gliadin proteins may also be used in this invention. Methods for producing recombinant gliadins have been described in the literature (Arentz-Hansen, E H, et al. Production of a panel of recombinant gliadins for the characterisation of T cell reactivity in coeliac disease. *Gut* 46: 46-51 (2000)). Preferred gluten-derived peptides of the invention comprise peptides of α-gliadin selected from the following peptides: 32-50, LGQQQPFPPQQPYPQPQPF (SEQ ID NO: 1); 32-44, LGQQQPFPPQQPY (SEQ ID NO: 2); 57-68, QLQPF-PQPQLPY (SEQ ID NO: 3); and 56-88, LQLQPF-PQPQLPYPQPQLPYPQPQLPYPQPQPF (SEQ ID NO: 4), or other suitable peptide of gluten (GenBank Accession No: AJ 133612) useful as a protein immunogen in accordance with the invention. In some publications, slightly different numbering systems are used and the peptide here called 56-88 is sometimes referred to as 57-89 (Shan, L, et al. Structural basis for gluten intolerance in Celiac Sprue. *Science* 297: 2275-9 (2002)). Gluten-derived peptides may be coupled to carrier proteins prior to immunizing the animals.

In other preferred embodiments the antibodies of the invention bind to a polypeptide having at least 80% sequence identity to a gluten protein or peptide including the peptides of SEQ ID NOS 1-4.

The present invention further relates to antibodies which immunospecifically bind gluten or gluten derived peptides. In addition to the monoclonal and polyclonal antibodies discussed above, antibodies of the invention also include, but are not limited to, multispecific, human, humanized or chimeric antibodies, single chain antibodies, Fab fragments, F(ab') fragments, F(ab')$_2$ fragments, fragments produced by a Fab expression library, and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibody fragments of the present invention include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are bovine, human, murine, rat, donkey, sheep, rabbit, goat, guinea pig, camel, horse, water buffalo, duck or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins.

The antibodies of the present invention may be monospecific, bispecific, trispecific or of greater multispecificity. Multispecific antibodies may be specific for different epitopes of a gluten or gluten-derived polypeptide or may be specific for both a gluten or gluten-derived polypeptide as well as for a heterologous epitope, such as a heterologous polypeptide or solid support material.

Antibodies of the present invention may also be described or specified in terms of their cross-reactivity. Antibodies that do not bind any other analog, ortholog, or homolog of a gluten or gluten-derived peptide are included. Antibodies that bind gluten or gluten derived polypeptides with at least 95%, at least 90%, at least 85%, at least 80%, at least 75%, at least 70%, at least 65%, at least 60%, at least 55%, and at least 50% identity (as is known in the art) to a gluten or gluten derived polypeptide of the present invention are also included in the present invention.

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; and WO 89/12624; U.S. Pat. No. 5,314,995; and EP 396,387.

The antibodies of the invention include derivatives that are modified, e.g., by the covalent attachment of any type of molecule to the antibody such that covalent attachment does not prevent the antibody from binding to the antigen. For example, but not by way of limitation, the antibody derivatives include antibodies that have been modified, e.g., by glycosylation, acetylation, PEGylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In one embodiment, the amino acid sequence of the heavy and/or light chain variable domains of an antibody in accordance with the invention may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes an antibody that specifically binds a gluten or gluten-derived polypeptide in accordance with the invention. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds.

CDRs may also be used in the generation of peptiomimietics and other similar agents that function in the same manner of an antibody of the invention. Peptidomimetics (molecules which are not polypeptides, but which mimic aspects of their structures to bind to the same site), are also suitable for use in the present invention. Peptidomimetics can be designed, for example, by establishing the three dimensional structure of the peptide agent in the environment in which it is bound or will bind to the gluten or gluten derived peptide. The peptidomimetic comprises at least two components, the binding moiety or moieties based on the CDRs and the backbone or supporting structure.

Examples of binding moieties suitable for use in designing a peptidomimetic for a basic amino acid in a peptide are nitrogen containing groups, such as amines, ammoniums, guanidines and amides or phosphoniums. Examples of binding moieties suitable for use in designing a peptidomimetic for an acidic amino acid can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, that provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, thereby forming a polyester backbone. In another embodiment, the carbonyl can be substituted with a sulfonyl group or sulfinyl group, thereby forming a polyamide. Reverse amides of the peptide can be made (e.g., substituting one or more —CONH— groups for a —NHCO— group). In yet another embodiment, the peptide backbone can be substituted with a polysilane backbone. These compounds can be manufactured by known methods.

Other compositions useful in the therapeutic and the diagnostic methods of the present invention are available to the skilled artisan and can be identified based upon their ability to function in a manner similar to that of the antibodies of the invention, for example to alter the metabolism of gluten in a celiac patient in a manner that protects the celiac patient from the toxic effects of gluten. It will be understood that appropriate agents able to alter the metabolism of gluten by celiac patients, may accomplish this effect in various ways. Without limitation to a particular theory, one class of agents will bind gluten and gluten-derived peptides with sufficient affinity and specificity to prevent uptake of gluten and gluten peptides in celiac patients, or inhibit the deamidation of gluten or gluten peptides by tissue transglutaminase, or inhibit the activation of the innate immune response by gluten peptides. In addition to the antibodies and peptidomimetics discussed above, a further example of an agent that can be used in the context of the present invention is a weakly basic anion exchange resin having a high selectivity for the adsorption of negatively charged deamidated gluten-derived that alters the metabolism of gluten in a celiac patient thereby protecting the patient from the toxic effects of gluten.

In one embodiment, to generate polyclonal antibodies on a large scale and at a low enough cost to be practical for the treatment of celiac disease, an appropriate animal species must be chosen. Polyclonal antibodies can be isolated from the milk or colostrum of immunized cows. Bovine colostrum contains 28 g of IgG per liter, while bovine milk contains 1.5 g of IgG per liter (Ontsouka, C E, et al. Fractionized milk composition during removal of colostrums and mature milk. J. Dairy Sci. 86:2005-2011 (2003)). Polyclonal antibodies can also be isolated from the yolk of eggs from immunized chickens (Sarker, S A, et al. Randomized, placebo-controlled, clinical trial of hyperimmunized chicken egg yolk immunoglobulin in children with rotavirus diarrhea. *J. Ped. Gastro. Nutr.* 32: 19-25 (2001)).

Multiple adjuvants are approved for use in dairy cows. Adjuvants useful in this invention include, but are not limited to, Emulsigen®, an oil-in-water emulsified adjuvant, Emulsigen®-D. an oil-in-water emulsified adjuvant with DDA immunostimulant, Emulsigen®-P, an oil-in-water emulsified adjuvant with co-polymer immunostimulant, Emulsigen®-BCL, an oil-in-water emulsified adjuvant with block co-polymer immunostimulant, Carbigen™, a carbomer base, and Polygen™, a co-polymer base. All of the listed adjuvants are commercially available from MVP Laboratories in Omaha, Nebr.

Antibodies useful in this invention can be identified in several different screening assays. First, antibodies are assayed by ELISA to determine whether they are specific for the immunizing antigen (a gluten protein or a gluten-derived peptide). Using standard techniques, ELISA plates are coated with immunogen, the antibody is added to the plate, washed, and the presence of bound antibody detected by using a second antibody specific for the Ig of the species in which the antibody was generated. An example of a typical gluten ELISA is given in Ellis et al, 1998. This assay is an initial screen to detect the presence of gluten specific antibody and to determine the relative concentration of antibody in the preparation. It may be preferable in this invention for the antibody preparation to contain antibodies specific for both gliadin and glutenin. This specificity can be determined with an ELISA, in which the binding of the antibody is measured using ELISA plate coated with gliadin or with glutenin.

Second, antibodies will be screened for their ability to inhibit tissue transglutaminase 2—mediated deamidation of a gluten-derived peptide using methods described in the literature (Shan, L, et al. Structural basis for gluten intolerance in Celiac Sprue. *Science* 297: 2275-9 (2002)). Most antibody preparations useful in this invention should inhibit the action of the enzyme on the peptide; however, antibodies raised by immunization of animals with a deamidated gluten or gluten-derived peptide may not inhibit tissue transglutaminase 2, and this assay would not be useful in the identification of such antibodies.

Third, a functional in vitro assay can be used to screen antibodies. A digest of gluten is prepared by incubating gluten with gastric proteases. This digest is then incubated with enzymes derived from rat small intestinal mucosal brush border membranes as described (Shan, L, et al. Structural basis for gluten intolerance in Celiac Sprue. *Science* 297: 2275-9 (2002)) and with tissue transglutaminase in the presence or absence of antibody. The inhibitory activity of the antibody is measured by determining whether the resulting mixture is able to stimulate T cell clones or lines specific for the toxic peptides from gluten.

Fourth, a second functional assay is used to determine whether the antibodies are able to inhibit activation of the innate immune system. Duodenal biopsy specimens from celiac disease patients will be incubated with the peptide 31-43 in the presence or absence of antibody and lymphocyte activation will be measured as described (Maiuri L, et al. Association between innate response to gliadin and activation of pathogenic T cells in coeliac disease. *Lancet*. 362:30-7 (2003)).

Any antibody useful in this invention will be active in the first assay, demonstrating binding specificity for gluten or gluten-derived peptides. The preferred antibodies will be active in the fourth assay, more preferably in the third and fourth, and most preferably in the second, third and fourth functional assays.

Oral delivery of protein therapeutics is challenging because the GI tract is designed to degrade and digest ingested material. However, it is possible to overcome these issues through formulation or by the careful choice of excipients. For example, milk-derived immunoglobulin has been used to protect against an oral challenge of enterotoxigenic *Escherichia coli*, an organism that infects the small intestine, by administering the immunoglobulin with sodium bicarbonate to neutralize stomach acids (Freedman, D J, et al. Milk immunoglobulin with specific activity against purified colonization factor antigens can protect against oral challenge with enterotoxigenic *Escherichia coli. J Infect. Dis.* 177: 662-7 (1998)). Furthermore, direct measurements of bovine immunoglobulin in illeal fluid in human subjects has shown that significant amounts of immunoglobulin survive transit through the stomach and small intestine (Wamy, M, et al. Bovine immunoglobulin concentrate-*Clostridium difficile* retains *C difficile* toxin neutralizing activity after passage through the human stomach and small intestine. *Gut,* 44:212-17 (1999)). Methods have also been described to formulate avian immunoglobulin (IgY) for GI delivery (Kovacs-Nolan, J and Mine, Y. Microencapsulation for the gastric passage and controlled intestinal release of immunoglobulin Y. *J. Immunol. Methods.* 296: 199-209 (2005)).

Polyclonal antibodies have been used to provide passive immunity against diarrhea caused by infectious agents. Most of these studies have been done using bovine antibodies isolated from either milk or colostrum. These infectious agents include rotavirus (Mitra, A K, et al. Hyperimmune cow colostrums reduces diarrhoea due to rotavirus: a double-blind, controlled clinical trial. *Acta Peadiatr.* 84: 996-1001 (1995)), *Clostridium difficile*, enterotoxigenic *Escherichia coli* (Freedman, D J, et al. Milk immunoglobulin with specific activity against purified colonization factor antigens can protect against oral challenge with enterotoxigenic *Escherichia coli*. *J. Infect. Dis.* 177: 662-7 (1998)), *Cryptosporidium* (Ungar, B L P, et al. Cessation of *Cryptosporidium*-associated diarrhea in an acquired immunodeficiency syndrome patient after treatment with hyperimmune bovine colostrum. *Gastroenterology.* 98: 486-9 (1990)), *Shigella flexneri* (Tacket, C O, et al. Efficacy of bovine milk immunoglobulin concentrate in preventing illness after *Shigella flexneri* challenge. *Am. J. Trop. Med. Hyg.* 47:276-83 (1992)). There has also been a report of treatment of rotavirus diarrhea using IgY isolated from the eggs of immunized chickens (Sarker, S A, et al. Randomized, placebo-controlled, clinical trial of hyperimmunized chicken egg yolk immunoglobulin in children with rotavirus diarrhea. *J. Ped. Gastro. Nutr.* 32: 19-25 (2001)) and a report of treating *H. pylori* with chicken IgY (Shin, J-H, et al. Production of anti-*Helicobacter pylori* urease-specific immunoglobulin in egg yolk using an antigenic epitope of *H. pylori* urease. *J. Med. Microbiol.* 53: 31-34 (2004)). In some of these cases (e.g., *C. difficile*), the antibodies are specific for a toxin produced by the pathogen. Therefore, it is known that an antibody, when delivered orally, can neutralize a toxin in the GI tract.

In accordance with one aspect of the invention, the invention provides a therapeutic composition comprising anti-gluten antibody suitable for delivery, preferably oral delivery, to a patient, preferably a human patient. The pharmaceutical composition may further comprise suitable carriers, adjuvants and other physiologically acceptable excipients.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate and-hydroxypropyl methylcellulose acetate succinate, methacrylate copolymers and cellulose acetate phthalate.

In accordance with another aspect of the invention, the invention provides a method of treating celiac disease or dermatitis herpetiformis in a human comprising administering to a patient a composition of the invention in an amount effective for treating said celiac disease or dermatitis herpetiformis. An "effective amount" is an amount sufficient to effect beneficial or desired clinical results. An effective amount can be administered in one or more administrations. In terms of treatment of celiac disease or dermatitis herpetiformis, an "effective amount" of an anti-gluten antibody is an amount sufficient to palliate, ameliorate, stabilize, reverse, slow or delay progression of the celiac disease or dermatitis herpetiformis condition in accordance with clinically acceptable standards for disorders to be treated or for cosmetic purposes.

The composition of the invention may be administered to a patient prior to, or concurrently with the ingestion of a substance that may contain gluten. The composition of the invention may be administered after ingestion of a substance containing gluten. The composition of the invention may be administered to the patient on a regular dosing schedule.

Detection and measurement of indicators of efficacy may be measured by a number of available diagnostic tools, including but not limited to, for example, by physical examination including blood tests, biopsies of the small intestine, pulmonary function tests, and chest X-rays; CT scan; bronchoscopy; bronchoalveolar lavage; lung biopsy and CT scan. Suppression of the deleterious T-cell activity can be measured by enumeration of reactive Th1 cells, by quantitating the release of cytokines at the sites of lesions, or using other assays for the presence of autoimmune T cells known in the art. Also both the physician and patient can identify a reduction in symptoms of a disease.

The pharmaceutical compositions of this invention comprise any of the compounds of the present invention, or pharmaceutically acceptable derivatives thereof, together with any pharmaceutically acceptable carrier. The term "carrier" as used herein includes known acceptable adjuvants and vehicles.

The pharmaceutical compositions of the invention are preferably administered to a patient orally. If given orally, they can be administered in any orally acceptable dosage form including, but not limited to, capsules, tablets, aqueous suspensions or solutions.

The dosage and dose rate of the compounds of this invention effective to produce the desired effects will depend on a variety of factors, such as the nature of the antibody, the size of the subject, the goal of the treatment, the nature of the pathology to be treated, the specific pharmaceutical composition used, and the judgment of the treating physician. Dosage levels of between about 0.1 and about 1000 mg/kg body weight per dose, preferably between about 1 and about 500 mg/kg body weight per dose of the active ingredient antibody are useful. Most preferably, the antibodies of the invention will be administered at a dose ranging between about 1 mg/kg body weight/dose and about 200 mg/kg body weight/dose, preferably ranging between about 5 mg/kg body weight/dose and about 50 mg/kg body weight/dose. Doses will be administered prior to or following ingestion of gluten or at intervals of every 2-8 hours.

The antibodies of this invention can also be useful in diagnostic applications. As capture or non-neutralizing antibodies, they can bind to gluten or gluten derived peptides without inhibiting partner binding and/or signaling. As neutralizing antibodies, they can be useful in competitive binding assays. They will also be useful in detecting or quantifying gluten or gluten-derived peptides.

U.S. Pat. No. 6,955,810, incorporated herein by reference, provides a general discussion of methods for the preparation of various types of monoclonal and polyclonal antibodies such methods being useful in the practice of the present invention. U.S. Pat. No. 6,955,810 also discloses methods for testing and assaying antibodies to determine if they have the desired biological effect, such methods also being useful in the practice of the present invention.

The following non-limiting Example is provided to illustrate the present invention.

Example 1

Generation of *Bovine* Gliadin-Specific Immunoglobulin

Whole wheat flour is purchased from Bob's Red Mill (Milwaukee, Wis.). Gliadin is isolated as described in Weiss, J B, et al. Gluten-sensitive enteropathy. Immunoglobulin G heavy-chain (Gm) allotypes and the immune response to wheat gliadin. *J. Clin. Invest.* 72:96-101 (1983). 20 g of flour is extracted with 200 mL of 55% ethanol at 40° C. for 60 min. The precipitate is removed by centrifugation at 19,000 g for 10 min. 600 mL of 1.5% NaCl is added to the supernatant and the precipitated gliadins are isolated by centrifugation at 25,000 g for 50 min. The precipitate is washed several times with 1.5% NaCl, dissolved in 0.01 M acetic acid, dialyzed against distilled water and lyophilized.

Gliadin is dissolved in PBS at 0.1 mg·mL and emulsified 1:1 (vol/vol) with Emulsigen®-D (purchased from MVP Laboratories, Omaha, Nebr.), an oil-in-water adjuvant containing an immunostimulant. Pregnant, healthy, mastitis-free Holstein dairy cows are immunized subcutaneously in the rear thigh with 100 µg of gliadin in a total volume of 2 mL. All vaccinations are performed under the direction of a licensed veterinarian and health records are maintained. Vaccinations are given on days 0, 21 and 35. The immunizations are timed such that the final boost is given approximately three weeks before parturition.

Colostrums are collected on days 1-4 after parturition. Colostrum is collected from each vaccinated cow separately and immediately frozen. Small (15 mL) samples of each milking are taken from cows prior to freezing bulk colostrum. These samples are used to measure immunogenicity of the vaccine regimen on an individual cow basis. Colostrums are pooled and frozen at −20° C. until further use.

Immune colostrum is processed into cheese by standard dairy practices. The whey fraction (containing the immunoglobulin) is pasteurized and fat is removed by centrifugation. Defatted whey is enriched for immunoglobulin by ion exchange chromatography and concentrated by hollow-fiber filtration. Phospholipids and residual non-immunoglobulin proteins are precipitated chemically and removed by continuous-flow centrifugation. The centrifugation supernatant is collected and concentrated to approximately 10% solids using the hollow-fiber filtration system. During this concentrating, residual lactose, milk peptides and other salts are removed by step-wise diafiltration against 3 volumes of 15 mM potassium citrate, pH 6.5. The buffered immunoglobulin is frozen and lyophilized to produce a stable, dry powder.

Anti-gluten antibody titers are determined by measuring the binding of bovine immunoglobulin to gluten protein-coated plates by ELISA using standard methods.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising an anti-gluten antibody and a pharmaceutically acceptable carrier wherein the antibody is isolated from milk or colostrum of a ruminant such as a cow, goat or sheep that has been immunized with an adjuvant in combination with gluten, gliadin, glutenin, a gluten derived peptide or any combination thereof and wherein the gluten-derived peptide is selected from the following α-gliadin peptides: LGQQQPFPPQQPYPQPQPF (SEQ ID NO: 1); LGQQQPFPPQQPY (SEQ ID NO: 2); QLQPFPQPQLPY (SEQ ID NO: 3); and LQLQPFPQPQLPYPQPQLPYPQPQLPYPQPQPF (SEQ ID NO: 4).

2. The pharmaceutical composition of claim 1 where the glutamine residues in the gluten, gliadin, glutenin or gluten-derived peptide have been partially or fully deamidated prior to immunization of the ruminant used to generate the anti-gluten antibody.

3. The pharmaceutical composition of claim 1 formulated for oral delivery to a patient.

4. A pharmaceutical composition comprising an isolated anti-gluten antibody and a pharmaceutically acceptable carrier wherein the anti-gluten antibody is specific for a toxic peptide from gluten wherein the toxic peptide derived from gluten is selected from the following α-gliadin peptides:

LGQQQPFPPQQPYPQPQPF;  (SEQ ID NO: 1)

LGQQQPFPPQQPY;  (SEQ ID NO: 2)

QLQPFPQPQLPY;  (SEQ ID NO: 3)
and

LQLQPFPQPQLPYPQPQLPYPQPQLPYPQPQPF.  (SEQ ID NO: 4)

5. The pharmaceutical composition of claim 4 wherein the antibody inhibits activation of the innate immune system.

6. The pharmaceutical composition of claim 4 wherein the antibody inhibits the stimulation of T cell clones or T cell lines specific for the toxic peptide.

7. The pharmaceutical composition of claim 4, wherein the anti-gluten antibody is present in the composition in a dosage range of 1 mg/kg-500 mg/kg body weight per dose.

8. The pharmaceutical composition of claim 4 wherein the anti-gluten antibody is isolated from milk.

9. A pharmaceutical composition comprising an anti-gluten antibody and a pharmaceutically acceptable carrier wherein the antibody is isolated from milk or colostrum and wherein the anti-gluten antibody is specific for a toxic peptide from gluten wherein the toxic peptide derived from gluten is selected from the following α-gliadin peptides: LGQQQPFPPQQPYPQPQPF (SEQ ID NO: 1); LGQQQPFPPQQPY (SEQ ID NO: 2); QLQPFPQPQLPY (SEQ ID NO: 3); LQLQPFPQPQLPYPQPQLPYPQPQLPYPQPQPF (SEQ ID NO: 4); and any combination thereof.

10. The pharmaceutical composition of claim 9, wherein the anti-gluten antibody is present in the composition in a dosage range of 5 mg/kg-50 mg/kg body weight per dose.

* * * * *

SEQUENCE LISTING

```
<160> NUMBER OF SEQ ID NOS: 4

<210> SEQ ID NO 1
<211> LENGTH: 19
<212> TYPE: PRT
<213> ORGANISM: Artificial Sequence
<220> FEATURE:
<223> OTHER INFORMATION: Recombinantly produced peptide of
      Triticumaestivum

<400> SEQUENCE: 1

Leu Gly Gln Gln Gln Pro Phe Pro Pro Gln Gln Pro Tyr Pro Gln Pro
1               5                   10                  15

Gln Pro Phe

<210> SEQ ID NO 2
<211> LENGTH: 13
<212> TYPE: PRT
<213> ORGANISM: Artificial Sequence
<220> FEATURE:
<223> OTHER INFORMATION: Recombinantly produced peptide of
      Triticumaestivum

<400> SEQUENCE: 2

Leu Gly Gln Gln Gln Pro Phe Pro Pro Gln Gln Pro Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Recombinantly produced peptide of
      Triticumaestivum
```

```
<400> SEQUENCE: 3

Gln Leu Gln Pro Phe Pro Gln Pro Gln Leu Pro Tyr
 1               5                  10

<210> SEQ ID NO 4
<211> LENGTH: 33
<212> TYPE: PRT
<213> ORGANISM: Artificial Sequence
<220> FEATURE:
<223> OTHER INFORMATION: Recombinantly produced peptide of
      Triticumaestivum

<400> SEQUENCE: 4

Leu Gln Leu Gln Pro Phe Pro Gln Pro Gln Leu Pro Tyr Pro Gln Pro
 1               5                  10                  15

Gln Leu Pro Tyr Pro Gln Pro Gln Leu Pro Tyr Pro Gln Pro Gln Pro
             20                  25                  30

Phe
```